United States Patent

Santa Ana, Jr.

Patent Number: 5,403,588
Date of Patent: Apr. 4, 1995

[54] DISPOSABLE BODY DEODORANT PAD AND DEODORANT PREPARATION THEREFOR

[76] Inventor: Cesareo T. Santa Ana, Jr., 806 N. Blvd., #7, Richmond, Va. 23220

[21] Appl. No.: 155,887

[22] Filed: Nov. 23, 1993

[51] Int. Cl.$^6$ .............................. A01N 25/34
[52] U.S. Cl. ...................... 424/402; 424/47; 424/68; 424/401; 424/685
[58] Field of Search ............ 424/402, 401, 65, 68, 424/47, 685; 604/359

[56] References Cited

U.S. PATENT DOCUMENTS

| | | | |
|---|---|---|---|
| 3,984,535 | 10/1976 | Ghilardi et al. | 424/47 |
| 4,719,101 | 1/1988 | Morrison | 424/65 |
| 4,877,605 | 10/1989 | Hendricks | 424/65 |
| 4,883,651 | 11/1989 | Meyer | 424/47 |
| 5,037,412 | 8/1991 | Tanzer et al. | 604/359 |

FOREIGN PATENT DOCUMENTS 17168  6/1984  Philippines.

*Primary Examiner*—Thurman K. Page
*Assistant Examiner*—Jyothsna Venkat
*Attorney, Agent, or Firm*—Christopher W. Brody

[57] ABSTRACT

A body deodorant composition consists essentially of a combination of 70% isopropyl alcohol, acetone and aluminum chloride in individual amounts which provide improved cleansing and deodorizing effects. The body deodorizing composition is incorporated into an absorbent cotton pad as a solution and packaged in individual pouches for use. Rubbing the saturated cotton pad effectively controls body odor through cleansing the skin and removing the substances thereon which contribute to body odor. The body deodorizing composition also restricts the excretion of body secretions to enhance the deodorizing effect.

12 Claims, 1 Drawing Sheet

DISPOSABLE BODY DEODORANT PAD AND DEODORANT PREPARATION THEREFOR

FIELD OF THE INVENTION

The present invention is directed to a disposable body deodorant pad and a deodorant preparation therefor and, in particular, a cotton absorbent pad saturated with a body deodorant preparation including a 70% isopropyl alcohol and acetone solution with aluminum chloride in specified amounts for improved control of body odor.

BACKGROUND ART

The cause of body odor is specifically related to the decomposition products resulting from the reaction which takes place on the surface of the skin between bacteria and certain body secretions called apocrine secretions. The apocrine secretion is a milkish, fatty fluid formed in the apocrine glands found in the deeper layers of the skin, most abundantly in the axilla or underarm area. This secretion is manufactured in the gland by a very slow continuous process but the discharge or excretion thereof from the skin's surface occurs intermittently subject to variables such as emotional stress, including fear and/or anger. However, after the gland has emptied its contents, further stress or stimulation is ineffective until a sufficient amount of secretion has again formed and accumulated inside the gland. The additional formation of the apocrine secretion usually take several hours after the gland has been depleted.

Other secreting glands of the skin called sebaceous or oil glands also produce a fatty substance called sebum which flows out over the skin surface and is responsible for the natural oiliness of skin. However, this oily substance mixes with dirt and bacteria on the skin and blends with the apocrine secretions. This combination of components forms an oily film which not only serves as a protective insulation for these substances but also tends to cling to the skin pores and irregularities so that their removal becomes relatively difficult.

The bacteria( population on the skin surface is another determining factor in body odor in that a sufficient level is required to bring about enough reaction with the apocrine secretions to produce perceptible odor.

Either bacteria alone or apocrine secretions alone is odorless. These two components must combine and react to produce the composition products which are actually the cause of body odor. Although the apocrine secretions, sebum, dirt and bacteria all play a roll in body odor, other physical and physiological factors can significantly modify the nature of the reaction between bacteria and apocrine secretions.

Various compositions, preparations and deodorant pads have been proposed in the prior art to control odors associated with the human body. U.S. Pat. No. 4,719,101 to Morrison discloses a deodorant composition which comprises a cosmetically acceptable vehicle containing methyl salicylate and a solubility enhancing oil, preferably peanut oil. The composition is externally applied to the skin, generally to the feet of a user and provides protection against development of odor.

U.S. Pat. No. 5,037,412 to Tanzer et al discloses an absorbent article designed for adsorbing and retaining human exudate. The absorbent article includes a deodorizing mixture which is an anhydrous, non-buffer blend of acidic, basic and pH neutral odor adsorbing particles.

It is also known to use aluminum chloride as a cosmetic astringent for perspiration control. U.S. Pat. No. 4,877,605 to Hendricks discloses an improvement over prior art aluminum chloride—containing perspiration control means. In this patent, a deodorant composition is disclosed as a foot deodorant comprising boric acid, hydrogen peroxide, sodium chloride, alcohol and water.

Prior art deodorant compositions and preparations still have drawbacks regarding control of body odor. Known body deodorant compositions that merely restrict the excretion of body secretions fail to effectively control bacteria or oil accumulation on the skin. Moreover, many deodorant compositions require daily use and include components or compounds that have been found to cause skin irritation. Other deodorizing compounds may be effective in removing some of the substances contributing to body odor but are ineffective in removing all of the body odor causing components.

In view of these drawbacks, a need has developed to provide an improved body deodorant composition or preparation and a method of applying it to human skin for effective body odor control. The present invention overcomes the drawbacks in the prior art by providing a disposable body deodorant composition, particularly for use with an absorbent pad which is effective in controlling bodily secretions and effectively cleanses the skin surface to provide effective body deodorant control over an extended period of time.

SUMMARY OF THE INVENTION

It is accordingly a first object of the present invention to provide an improved body deodorant composition and, in particular, a body deodorant composition for use with an absorbent pad.

Another object of the present invention is to provide a method of controlling body odor using a body deodorant-containing absorbent pad which controls body odor over an extended time period.

A further object of the present invention is to provide a disposable body deodorant composition and deodorant pad which effectively controls bacteria, dirt and bodily secretions simultaneously for improved deodorant control.

Other objects and advantages of the present inventions will become apparent as a description thereof proceeds.

In satisfaction of the foregoing objects and advantages, the present invention provides a body deodorant composition consisting essentially of a mixture of 70% solution of isopropyl alcohol and acetone as a solution with aluminum chloride.

Preferably, 115 to 125 cc's of the 70% solution of isopropyl alcohol are mixed with 5 to 15 cc's of acetone to form a solution, 88.5 to 96.2% 70% isopropyl alcohol by volume with 3.8 to 11.5% acetone by volume. Aluminum chloride is added to the solution in amounts ranging between 3.35 to 3.7% by weight.

More preferably, 120 cc's of the 70% isopropyl alcohol component are mixed with 10 cc's of acetone to form a solution wherein 3.6 grams of aluminum chloride are added thereto.

The inventive body deodorant composition can be incorporated as a solution in an absorbent material such as cotton for application to human skin. When applying the body deodorant composition, a solution of the aluminum chloride, acetone and 70% isopropyl alcohol is prepared in the amounts disclosed above. The cotton absorbent pad is saturated with the solution and packaged in a plastic or plasticized aluminum foil pouch as disposable units. In use, the saturated cotton pad is removed from the pouch and rubbed on the skin, preferably in the underarm area. The rubbing action provides a cleansing function of unwanted agents of the skin surface. Any oils that may be on the skin surface are dissolved by the solvents with the astringent component providing an inhibiting function of further excretion of body secretions.

BRIEF DESCRIPTION OF THE DRAWINGS

Reference is now made to the sole drawing accompanying the invention wherein a perspective view of an absorbent pad containing the inventive body deodorant composition is illustrated in conjunction with a pouch for storage thereof prior to use.

DESCRIPTION OF THE PREFERRED EMBODIMENTS

Figure 1:
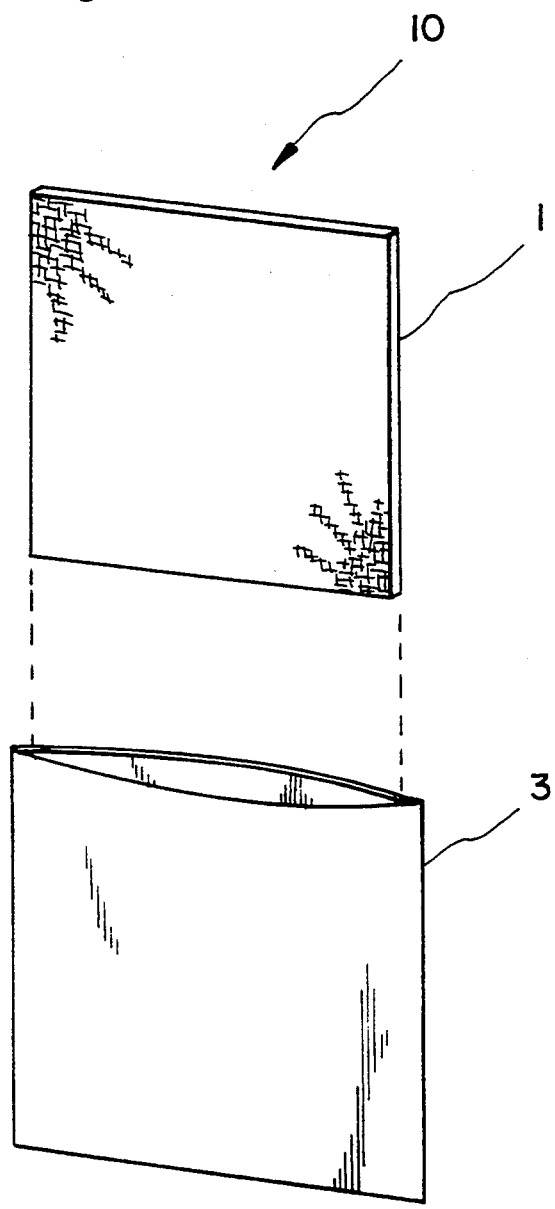

The present invention provides improvements over other prior art body deodorizing compounds and systems. The inventive combination, by combining a solvent, antiseptic and astringent, cleanses, attacks germs, checks perspiration and deodorizes simultaneously. Thus, the inventive body deodorant composition and pad may be used without previous bathing.

Due to the unique makeup of the body deodorant composition, the deodorizing effect can last up to three to four days before reapplication is necessary.

The inventive composition also uses a lower amount of the antiperspirant or astringent component, thereby reducing potential skin irritation. The body deodorant composition can be effectively used in solution form. In this manner, individual and disposable pads can be saturated with the deodorizing solution and packaged in individual units for convenient use.

The inventive body deodorant is different from other existing and known body deodorants by its unique combination of deodorizing components. The inventive body deodorant composition employs solvent agents which thin out and render more fluid the oily film in which bacteria and apocrine secretions are held. The solvent agents permit more effective and complete physical removal of this oily film. The solvent agent also provides better penetration by the antiseptic component of the body deodorizing compound.

The absorbent cotton pad adsorbs and also physically removes more of the unwanted substances from the skin. The more of the existing bacteria and apocrine secretions that are removed, the longer it takes for them to build up again and produce the necessary action that leads to body odor.

The astringent component of the inventive composition further restricts secretions of the sweat glands and delays their build up. This astringent component augments the affect of delaying the build up of unwanted substances on the skin to an optimal level through use of the solvents, antiseptic and cotton pad.

The inventive body deodorant composition consists essentially a solution of 70% isopropyl alcohol, acetone and aluminum chloride. More preferably, the acetone and 70% isopropyl alcohol are formed as a solution first consisting essentially of about 88.5 to 96.2% by volume of a 70% solution of isopropyl alcohol as both a solvent and antiseptic and about 3.8% to 11.5% acetone as a solvent. Finally, aluminum chloride is provided in amounts ranging from about 3.3 to 3.8% by weight of the solution, the density of the 70% isopropyl alcohol and acetone being approximately 0.8 gm/cc.

Isopropyl alcohol is a known antiseptic as well as a solvent for fats, oils and waxes. Acetone is also a known solvent for fats, oils and waxes. Using isopropyl alcohol in a 70% solution as both an antiseptic and a solvent reduces the concentration of acetone and its attendant irritating effect.

More preferably, the body deodorant composition comprises a solution of 92.3% 70% isopropyl alcohol, and 7.7% acetone by volume. Aluminum chloride is added to the solution such that the aluminum chloride is about 3.3% by weight of the solution.

For example, 115 to 125 cc's of 70% isopropyl alcohol is added to 5 to 15 cc's of acetone to form a solution comprising about 130 cc's in volume. To this amount is added 3 to 4 grams of aluminum chloride, which readily dissolves in the acetone-isopropyl alcohol solution. Most preferably, 120 cc's of 70% isopropyl alcohol, 10 cc's of acetone and 3.6 grams are aluminum are mixed together to form the deodorant preparation or 92.3% 70% isopropyl alcohol and 7.7% acetone by volume as a solution with 3.34% by weight of aluminum chloride added thereto.

The aluminum chloride or astringent (anti-perspirant) component is used in a reduced amount compared to typical prior art strengths of 10%. A much lesser amount of the aluminum chloride component is needed due to the synergistic action of the combined ingredients of the body deodorant composition. Furthermore, the inventive body deodorant composition, by delaying the build-up of sebaceous and apocrine secretions to levels that result in offensive body odor, does not require complete suppression of sweating by an astringent. Aluminum chloride is also preferred because it is soluble in both alcohol and acetone.

The absorbent pad can be any absorbent material capable of providing a cleansing action when rubbed against human skin. Preferably, the absorbent material is cotton since it functions as both a cleansing agent and an absorber.

The cleansing action associated with the body deodorant composition, including both the wiping action of the cotton against skin as well as the dissolving functions of the solvents plays an important role in the overall synergistic effect of the invention. The antiseptic-solvent-absorbent cotton complex removes chemically and physically the offending material, thus cleansing much more effectively than ordinary soap and water. This is advantageous over current existing body deodorants in that the inventive body deodorant body composition can be effectively used without previous bathing. With prior art compositions, the skin must be cleansed before application of the anti-perspirant or deodorant.

The unique combination of the solvent, antiseptic and cleansing components also results in a lesser concentration of each component, which in turn, lessens or totally removes any adverse effects, particularly skin irritation associated with individual components.

The body deodorizing composition is preferably prepared as a solution in the proportions set forth above. An absorbent cotton pad is saturated with the solution and individually sealed in a packet such as a plastic pouch or plasticized aluminum foil pouch. With reference now to the sole Figure, the invention is generally designated by the reference numeral 10 and includes an absorbent cotton pad removed from a pouch sized for retaining an individual pad. As can be seen from the sole Figure, the absorbent cotton pad 1 is rectangular in shape. The retaining pouch 3 is also rectangular in shape to provide a compact and individual unit for a user.

In use, the absorbent cotton pad 1 is removed from the packet 3 and rubbed against the skin portion where body odor control is desired. Typically, the adsorbing cotton pads can be used on the underarms. More preferably, the adsorbing cotton pads are sized approximately 2½×1½ inches with a thickness of 3/16 inches.

It should be understood that other sizes can be utilized for the disclosed absorbent cotton pads as well as other absorbent materials such as paper products or synthetic fiber materials. Although the deodorant composition has been particularly disclosed as a solution for use with an absorbent pad, the composition may also be applied by other means such as a roll-on dispenser or spray. Preferably, if the deodorant composition is applied in this manner, the applied composition should be removed by using a cotton pad or the like to obtain the full benefit of the synergistic combination of the cleansing action described above.

As such, an invention has been disclosed in terms of preferred embodiments thereof which fulfill each and every one of the objects of the present invention as set forth hereinabove and provide a new and improved body deodorant composition pad and method of application.

Various changes, modifications and alterations from the teachings of the present invention may be contemplated by those skilled in the art without departing from the intended spirit and scope thereof. Accordingly, it is intended that the present invention only be limited by the terms of the appended claims.

I claim:

1. A disposable body deodorant pad comprising an absorbent material containing a body deodorant solution consisting essentially of:
   a solution of 88.5 to 96.2% of a 70% isopropyl alcohol solution and 3.8 to 11.5% acetone by volume, and 3.3 to 3.8% aluminum chloride by weight of said solution.

2. The disposable body deodorant pad of claim 1 wherein said absorbent material is cotton.

3. The disposable body deodorant pad wherein said body deodorant solution consists essentially of:
   a solution of 92.3% of a 70% isopropyl alcohol solution and
   7.7% acetone by volume; and
   3.34% aluminum chloride by weight of said solution.

4. The disposable body deodorant pad of claim 1, wherein said absorbent material is in a non-porous polymer containing aluminum foil pouch.

5. The disposable body deodorant pad of claim 4 wherein said absorbent pad comprises cotton and is rectangular in shape.

6. A method of deodorizing at least a portion of a human body comprising the steps of:
   a) providing an absorbent pad containing a body deodorant solution consisting essentially of
      a solution of 88.5 to 96.2% of a 70% isopropyl alcohol solution and 3.8 to 11.5% acetone by volume; and
      3.3 to 3.8% aluminum chloride by weight of said solution; and
   b) applying said absorbent pad to said portion of said human body to remove dirt and bacteria therefrom and inhibit secretions of bodily fluids contributing to body odor therefrom.

7. The method of claim 6 wherein step (b) is repeated using another absorbent pad after lapse of a predetermined time.

8. The method of claim 5 wherein said body deodorant solution consists of:
   a solution of 92.3% of a 70% isopropyl alcohol solution and
   7.7% acetone by volume; and
   3.34% aluminum chloride by weight of said solution.

9. The method of claim 6 further comprising the steps of:
   i) providing said absorbent pad in an polymer-containing aluminum foil pouch; and
   ii) removing said absorbent pad from said pouch prior to said applying step.

10. The method of claim 6 wherein a cotton pad is provided as said absorbent pad.

11. A body deodorant solution consisting essentially of:
    a solution of 88.5 to 96.2% of a 70% isopropyl alcohol solution, and 3.8 to 11.5% acetone by volume, and
    3.3 to 3.8% aluminum chloride by weight of said solution.

12. The disposable body deodorant pad solution of claim 11 consisting essentially of:
    a solution of 92.3% of a 70% isopropyl alcohol solution and
    7.7% acetone by volume; and
    3.34% aluminum chloride by weight of said solution.

* * * * *